United States Patent [19]

Yoswein-McGreen

[11] Patent Number: 5,228,142
[45] Date of Patent: Jul. 20, 1993

[54] OVERWRAP FOR FINGERS AND HANDS AND METHOD FOR USING IT

[76] Inventor: Rebecca Yoswein-McGreen, 260 Harrison Ave., Apt. 507, Jersey City, N.J. 07304

[21] Appl. No.: 568,354

[22] Filed: Aug. 16, 1990

[51] Int. Cl.⁵ .......................................... A41D 19/00
[52] U.S. Cl. ........................................ 2/169; 2/159; 2/21; 602/63
[58] Field of Search ............... 2/161 R, 163, 169, 165, 2/21, 20, 159, 161 R, 163, 21; 66/174; 604/290, 292; 602/79, 63

[56] References Cited

U.S. PATENT DOCUMENTS

| | | | |
|---|---|---|---|
| 474,929 | 5/1892 | Tabor et al. | 2/163 |
| 651,701 | 6/1900 | Delamere | 2/159 |
| 695,586 | 3/1902 | Steele | 2/166 |
| 883,452 | 3/1908 | Corliss | 2/21 X |
| 1,358,824 | 11/1920 | Burden | 2/163 |
| 2,416,800 | 3/1947 | Moller | 128/133 |
| 2,561,863 | 7/1951 | Holm | 128/157 |
| 2,633,126 | 3/1953 | Newmark | 2/21 X |
| 4,045,824 | 9/1977 | Weppler | 2/163 |
| 4,131,952 | 1/1979 | Brenning, Jr. | 2/161 R X |
| 4,748,693 | 6/1988 | Shinn | 2/161 R X |
| 4,947,486 | 8/1990 | Hsuih | 2/169 X |
| 4,964,174 | 10/1990 | Martin | 2/163 X |

FOREIGN PATENT DOCUMENTS 1342888 10/1963 France .
0002756 1/1985 Japan .

OTHER PUBLICATIONS

Spock, *Dr. Spock's Baby and Child Care*, p. 633 (1985).
Aaron et al., First Aid and Emergency Care Prevention and Protection of Injuries, pp. 317-318 (1972).

*Primary Examiner*—Werner H. Schroeder
*Assistant Examiner*—Sara M. Current
*Attorney, Agent, or Firm*—Gottlieb, Rackman & Reisman

[57] ABSTRACT

A glove-shaped overwrap of, e.g, cotton has finger portions which extend radially outwardly from a central hand portion. Ravel-stop means, e.g. baste stitches, encircle each of the finger portions adjacent the hand portion. A drawstring or other means permits the overwrap to be secured about the patient's wrist.

Where a patient's finger is to be bandaged or medicated, the other finger portions are severed from the hand portion. The finger is bandaged or medicated and the overwrap is then put on the bandaged or medicated hand so that the bandaged or medicated finger is covered by the unsevered finger portion of the overwrap. The drawstring is tied around the patient's wrist. The invention facilitates bandaging and medication of, e.g., infant fingers and hands, since infants tolerate the overwrap well and can neither remove the bandage from the finger nor eat or otherwise remove the medication from it.

2 Claims, 1 Drawing Sheet

ND METHOD FOR USING IT

OVERWRAP FOR FINGERS AND HANDS AND METHOD FOR USING IT

BACKGROUND OF THE INVENTION

The invention relates to bandages, medication and methods for bandaging and/or medicating wounds. More specifically, the invention relates to bandages and treatment methods for use on the hand and fingers. In its most immediate sense, the invention relates to bandages and treatment methods for use on infants with hand wounds, infections, etc.

It has long been known that it is difficult to bandage fingers and that it is especially difficult to bandage children's fingers and hands. Children do not tolerate bandages well and therefore try to remove them. It is thus frequently necessary to use oversize bandages and excessive quantities of surgical tape merely to insure that the bandages remain in place. This is not only difficult and wasteful but is also uncomfortable for the child.

The same difficulties are presented when it is necessary to medicate an infant's hand or finger. The infant frequently eats or otherwise removes the medication, thereby retarding the healing process.

In accordance with the invention, there is provided an overwrap for finger and hand injuries. The injuries may be covered by bandages or may be spread with medication. The overwrap is glove-shaped, and is made of light and air-permeable material, to promote healing. Ravel-stop means is located at the proximal end of each of the finger portions of the overwrap, adjacent the central hand portion, and means are provided for securing the overwrap around the patient's wrist.

When, e.g. the patient's index finger is to be bandaged or medicated, all other finger portions are severed from the hand portion. Then, after the bandage or medication has been applied to the finger, the overwrap is put on the hand and the unsevered finger portion is slipped over the bandage or medicated region. (When the hand alone is to be bandaged or medicated, all the finger portions are severed and the overwrap is then slipped over the bandaged or medicated hand.) The overwrap is then secured around the patient's wrist, so that it cannot be easily taken off. The ravel-stop means prevents the hand portion from unravelling where the severed finger portions have been cut off.

Advantageously, the overwrap is made of cotton. This makes it washable during the healing process and inexpensive enough to discard after healing is finished. Further advantageously, the securing means is a ribbon-like drawstring, which permits removal and repositioning of the overwrap to, e.g., change bandaging or apply medication. Still further advantageously, the drawstring is located so that it is tied at the medial side of the wrist. This makes it difficult for a child to untie it so as to remove the bandage.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
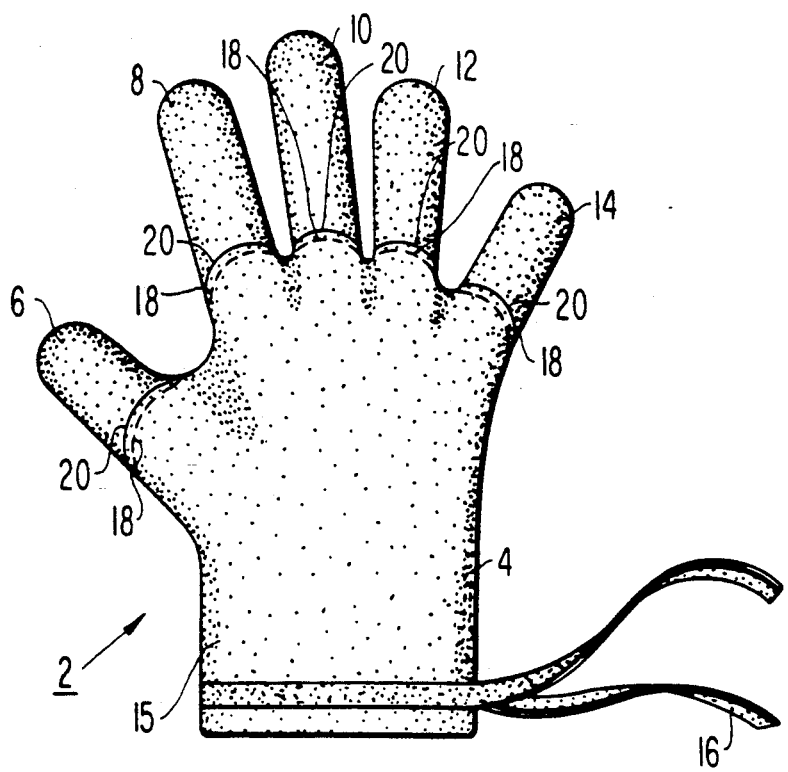
FIG. 1 is a drawing of a preferred embodiment of the invention.

An overwrap generally indicated by reference numeral 2 is dimensioned to fit over an infant's hand (not shown in FIG. 1). Snugness is to be avoided, since it is uncomfortable for the patient, but the overwrap should generally conform to the hand without constriction; if the fit is too loose, the overwrap can be removed. While the overwrap 2 may be so made as to fit only the right hand or only the left hand, it is presently considered advantageous if the overwrap 2 is shaped so that it can fit either the right or the left hand. This reduces the number of patterns which must be produced and increases the production volume for each pattern in production.

The overwrap 2 is made of a light and air-permeable material, stretchable cotton being presently preferred for reasons set forth below. Air-permeability is necessary to promote healing of the injured body part and lightness is preferred because it is more comfortable to the patient and because it is easier to cut light material.

The overwrap 2 has a central hand portion 4 and five outwardly extending finger portions 6 (thumb portion), 8 (index finger portion), 10 (middle finger portion), 12 (ring finger portion) and 14 (little finger portion). A wrist portion 15 extends from the hand portion 4, and at the distal end of the wrist portion 15 is a ribbon-like drawstring 16. The drawstring 16 is positioned so that it is tied at the medial side of the wrist (not shown).

Ravel-stop means 18 extends around each finger portion 6–14 at its junction with the hand portion 4. Where the material used for the overwrap 2 is stretchable cotton, the ravel-stop means 18 may be a band of stitching, such as basting stitches or stretch stitches such as are sewn by sewing machines. Alternatively, and depending upon the nature of the material used for the overwrap 2, the ravel-stop means 18 can be a ring of impregnated flexible rubber material, a ring of tape etc. The ravel-stop means 18 serves to prevent unravelling of the hand portion 4 where one of the finger portions 6–14 has been severed along line 20.

Figure 2:
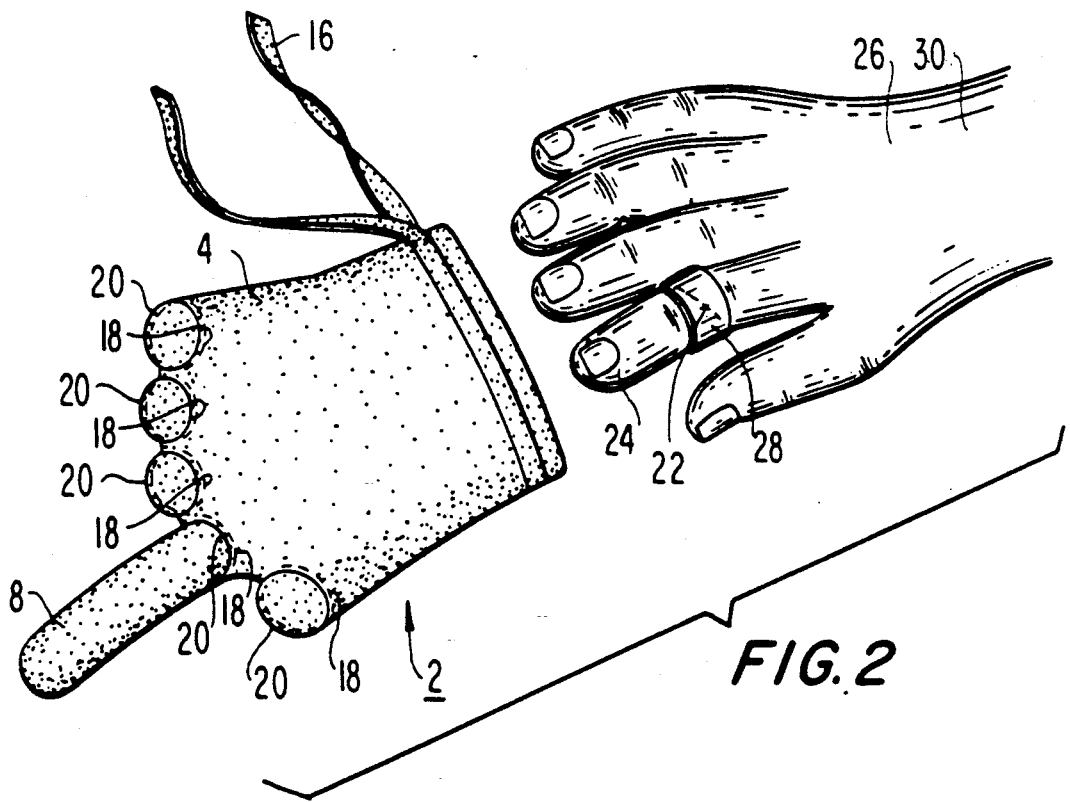
FIG. 2 illustrates bandaging a patient's finger in accordance with the invention.

In FIG. 2, an infant has a cut 22 on the index finger 24 of the right hand 26. After applying any necessary medication (not shown), a small bandage 28 is applied to the index finger 24 to cover the cut 22. Finger portions 6, 10, 12 and 14 are severed from the hand portion 4 along lines 20 and the remaining portions of the overwrap 2 are slipped over the infant's hand 26. The overwrap 2 is held in place by tying the drawstring 16 so that the wrist portion 14 is secured around the patient's wrist 30.

It will be evident that the unsevered finger portion 8 of the overwrap 2 covers the bandage 28. This prevents the infant from getting at, and therefore from removing, the bandage 28. Furthermore, the patient is prevented from eating or otherwise removing any medication which may have been applied to the index finger 24. The ravel-stop stitching bands 18 prevent unravelling from taking place where a finger portion 6, 10, 12 and 14 has been severed from the hand portion 4.

Infants tolerate the overwrap 2 well, presumably because it does not excessively limit finger motion. Additionally, infants do not appear to suck their fingers as much as they do when exposed bandages are utilized. The overwrap 2 may be removed and replaced by untying and retying the drawstring 16, to facilitate rebandaging and reapplication of medication. Where the overwrap 2 is made of cotton, it may be washed to remove e.g. dirt and dried blood when it has been removed during rebandaging and remedication.

While the preferred embodiment is particularly advantageous in the case of bandaged hands, it will be understood that the use of bandages is not necessary to the practice of the invention. The overwrap 2 serves equally well to prevent an infant from eating or otherwise removing medication not covered by a bandage.

It will be understood that the invention is not limited to pediatric use. It may also be used for adults, especially geriatric and mentally ill patients.

Although a preferred embodiment has been described above, the scope of the invention is limited only by the following claims:

I claim:

1. A method of treating infant patients with hand conditions, comprising the following steps:

procuring an overwrap comprising a glove-shaped element sized for an infant's hand and made of light, air-permeable material, the element having five finger portions extending outwardly from a central hand portion, ravel-stop means extending around each finger portion at its junction with the hand portion and means for securing the glove around the wrist of a patient;

severing, at such a location as to leave the ravel-stop means attached to the hand portion, each finger portion which corresponds to a patient's finger from which bandages are to be absent;

bandaging the patient's hand condition;

pulling the overwrap over the patient's bandaged hand; and securing the overwrap around the patient's wrist.

2. A method of treating infant patients with hand conditions, comprising the following steps:

procuring an overwrap comprising a glove-shaped element sized for an infant's hand and made of light, air-permeable material, the element having five finger portions extending outwardly from a central hand portion, ravel-stop means extending around each finger portion at its junction with the hand portion and means for securing the glove around the wrist of a patient;

severing, at such a location as to leave the ravel-stop means attached to the hand portion, each finger portion which corresponds to a patient's finger from which medication is to be absent;

medicating the patient's hand condition;

pulling the overwrap over the patient's medicated hand; and securing the overwrap around the patient's wrist.

* * * * *